United States Patent [19]

Cale, Jr.

[11] 4,296,037

[45] Oct. 20, 1981

[54] 4,5-DIHYDRO-3,3-DIPHENYL-4-HYDROCARBYLAMINOMETHYLFURAN-2(3H) ONES

[75] Inventor: Albert D. Cale, Jr., Mechanicsville, Va.

[73] Assignee: A. H. Robins Company, Incorporated, Richmond, Va.

[21] Appl. No.: 127,001

[22] Filed: Jul. 24, 1978

Related U.S. Application Data

[62] Division of Ser. No. 615,951, Sep. 23, 1975, Pat. No. 4,119,637.

[51] Int. Cl.$^3$ .......................................... C07D 307/26
[52] U.S. Cl. .................................................. 260/343.6
[58] Field of Search ...................................... 260/343.6

[56] References Cited

U.S. PATENT DOCUMENTS 2,490,937 12/1949 Weston .............................. 260/343.6
2,650,231 8/1953 Arnold et al. ..................... 260/343.6

OTHER PUBLICATIONS

Dangyan et al., Chem. Abst., vol. 71, 1969, 60636n.

*Primary Examiner*—Henry R. Jiles
*Assistant Examiner*—Jane T. Fan

[57] ABSTRACT

1-Hydrocarbon-3,3-diphenyl-4-hydroxymethyl-2-pyrrolidinones and methods for making them from 4,5-dihydro-3,3-diphenyl-4-hydrocarbylaminomethylfuran-2(3H)ones are disclosed. Methods for making the 4,5-dihydro-3,3-diphenyl-4-hydrocarbylaminomethylfuran-2(3H)ones are also disclosed. The novel compounds are useful intermediates for the preparation of pharmacologically active 4-(4,4-disubstitutedpiperidinylmethyl)-3,3-diphenyl-2-pyrrolidinones.

6 Claims, No Drawings

4,5-DIHYDRO-3,3-DIPHENYL-4-HYDROCARBYLAMINOMETHYLFURAN-2(3H) ONES

This is a division of application Ser. No. 615,951, filed Sept. 23, 1975, now U.S. Pat. No. 4,119,637, issued Oct. 10, 1978.

This invention relates to novel 2-pyrrolidinones and more particularly to 1-hydrocarbon-3,3-diphenyl-4-hydroxymethyl-2-pyrrolidinones having the formula:

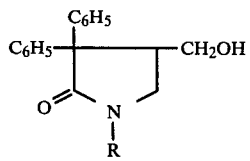

Formula I wherein R is lower-alkyl, lower cycloalkyl, and phenyl-lower alkyl.

The invention is also concerned with novel tetrahydrofuran-2-ones, especially 4,5-dihydro-3,3-diphenyl-4-hydrocarbylaminomethylfuran-2(3H)ones having the formula:

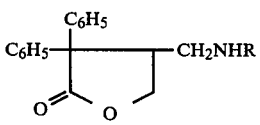

Formula II wherein R is lower alkyl, lower cycloalkyl and phenyl-lower alkyl.

The invention also relates to novel processes for preparing the novel compounds of Formulae I and II and to novel compounds which can be prepared from the compounds of Formula I.

The novel compounds of Formula I are particularly useful as intermediates for the preparation of a series of novel 4-(4-disubstituted-piperidinylalkyl)-3,3-diphenyl-2-pyrrolidinones wherein alkyl is methyl having analgetic and antidiarrheal properties disclosed in copending application Ser. No. 615,952 filed on even date herewith.

The novel 4,5-dihydro-3,3-diphenyl-4-hydrocarbylaminomethylfuran-2(3H)ones of Formula II are useful as precursors for the novel 1-hydrocarbon-3,3-diphenyl-4-hydroxymethyl-2-pyrrolidinones of Formula I. The compounds also form fluosilicic acid addition salts which are useful as mothproofing agents according to U.S. Pat. Nos. 1,915,334 and 2,075,359.

It is, accordingly, an object of the present invention to provide novel and useful 1-hydrocarbon-3,3-diphenyl-4-hydroxymethyl-2-pyrrolidinones. A further object is to provide novel and useful 4,5-dihydro-3,3-diphenyl-4-hydrocarbylaminomethylfuran-2(3H)ones. A still further object is to provide novel processes for the preparation of the novel 1-hydrocarbon 3,3-diphenyl-4-hydroxymethyl-2-pyrrolidinones and 4,5-dihydro-3,3-diphenyl-4-hydrocarbylaminomethylfuran-2(3H)ones. Other objects of the invention will be apparent to one skilled in the art, and still other objects will become apparent hereinafter from the description which follows and the appended claims.

The term "lower-alkyl" as used herein includes straight and branched chain radicals of up to six carbon atoms inclusive and is exemplified by such groups as methyl, ethyl, propyl, butyl, isopropyl, isobutyl, tertiary butyl, amyl, hexyl and isohexyl.

The term "phenyllower-alkyl" as used herein includes radicals such as benzyl, phenethyl, phenpropyl and α-methylbenzyl.

The term "lower cycloalkyl" as used herein includes cycloalkyl radicals having four to eight carbon atoms such as cyclobutyl, cyclopentyl, cyclohexyl, cycloheptyl and cyclooctyl, cyclopentyl and cyclohexyl being preferred radicals.

The novel compounds of Formula I are prepared by the following procedure:

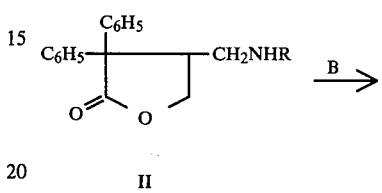

II

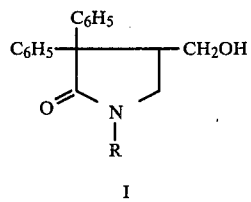

I wherein R is as defined above and B is a basic catalyst.

According to the above procedure a 4,5-dihydro-3,3-diphenyl-4-hydrocarbylaminomethylfuran-2(3H)one II is mixed with a catalytic amount of a strong base such as an alkali metal hydride, an alkali metal amide, an alkali metal tertiary butoxide or an alkali metal hydroxide, an alkali metal hydride being preferred, to cause intramolecular rearrangement to the 1-hydrocarbon-3,3-diphenyl-4-hydroxymethyl-2-pyrrolidinone I. The novel intramolecular rearrangement is usually carried out with the application of heat, e.g., in refluxing isooctane, benzene, toluene, or like solvent, for an extended period, e.g., of from about 10 to about 20 hours. The pyrrolidinone generally separates from the cooled reaction mixture as a crystalline solid which is isolated by filtration and is further purified by crystallization from a suitable solvent or solvents.

The novel compounds of Formula II are prepared by the following procedure:

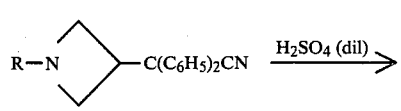

III

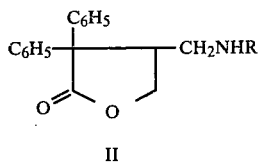

II wherein R is as defined above.

According to the above procedure an α,α-diphenyl-α-(1-hydrocarbon-3-azetidinyl)acetonitrile is reacted with dilute sulfuric acid resulting in the formation of the 4,5-dihydrofuran-2-(3H)one ring. The novel reaction is usually carried out with the application of heat, e.g., at a temperature of from about 110° C. to about 140° C. for an extended period, e.g., of from about 35 hours to about 60 hours to effect the formation of the 4,5-dihydro-3,3-diphenyl-4-hydrocarbylaminomethylfuran-2(3H)one II from the α,α-diphenyl-α-(1-hydrocarbon-3-azetidinyl)acetonitrile. The product can be obtained from the reaction mixture by various methods but is preferably isolated by pouring the acidic reaction mixture onto ice, separation of the aqueous-organic layers, acid-base extraction of the organic layer and recrystallization of the 4,5-dihydrofuran-2(3H)one product from a suitable solvent.

The α,α-diphenyl-α-(1-hydrocarbon-3-azetidinyl)acetonitriles III are prepared from 1-hydrocarbon-3-azetidinols by the following procedure:

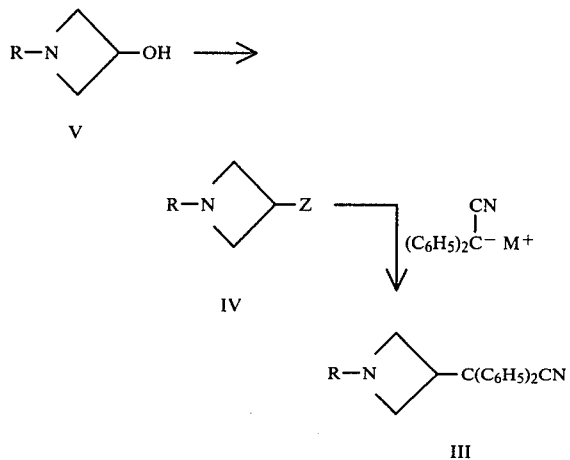

wherein R is as defined hereinabove, Z is a lower alkylsulfonyloxy radical, an arylsulfonyloxy radical or a halide radical, preferably chloride, and M+ is an alkali metal cation, preferably sodium or potassium.

According to the above procedure an alkyl or aryl sulfonate ester IV or an azetidinyl halide IV is prepared by methods known to the art. The alkali metal salt of diphenylacetonitrile is prepared in a similar solvent by reacting diphenylacetonitrile with an alkali metal hydride or an alkali metal amide. The sodium and potassium metal hydrides and amides are preferred. The solution of the alkyl or aryl sulfonate ester or the azetidinyl halide is then reacted with the alkali metal salt of diphenylacetonitrile at an elevated temperature, preferably at the reflux temperature of the organic solvent used. The α,α-diphenyl-α-(1-hydrocarbon-3-azetidinyl)acetonitrile III thusly prepared is isolated from the reaction mixture by known procedures and further purified by crystallization from a suitable solvent or solvents.

The 1-hydrocarbon-3-azetidinols are known compounds or they can be prepared as described by V. R. Gaertner, Tetrahedron Letters No. 39, pp. 4691-4 (1966), by Okutani et al., Chem. Pharm. Bull. 22 (7) 1490-7 (1974), or by procedures disclosed in U.S. Pat. No. 3,668,196.

The 1-hydrocarbon-3,3-diphenyl-4-halomethyl-2-pyrrolidinones of Formula VI

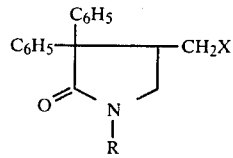

wherein R is as defined above and X is chloro, bromo or iodo are novel compounds and are readily prepared from the precursor hydroxy compounds. Thus, a 4-bromomethyl-3,3-diphenyl-1-isopropyl-2-pyrrolidinone can be prepared according to the procedure of Example 5 by substituting thionyl bromide for thionyl chloride. The 4-iodomethyl compound can be prepared by reacting a 4-chloromethyl compound with sodium iodide in acetone.

The α,α-diphenyl-α-(1-hydrocarbon-3-azetidinyl)acetonitriles disclosed herein as well as the α,α-diphenyl-α-(1-hydrocarbon-3-azetidinyl)acetamides prepared from them by partial hydrolysis in concentrated sulfuric acid have antiarrhythmic properties.

The following preparations and examples are not limiting but are illustrative of the compounds of this invention and processes for their preparation.

PREPARATION 1

α,α-Diphenyl-α-(1-isopropyl-3-azetidinyl)acetonitrile

A mixture of 168 g. (0.87 mole) of diphenylacetonitrile and 40.42 g. (0.96 mole) of 57% sodium hydride in one liter of dry toluene was stirred at reflux temperature for three hours.

A stirred solution of 1-isopropyl-3-azetidinol (100 g., 0.87 mole) and 101 g (1.0 mole) of triethylamine in 300 ml. of dry benzene was treated dropwise with 100 g. (0.87 mole) of methylsulfonyl chloride and after stirring for two hours at room temperature the mixture was filtered and the filter cake was washed with dry benzene.

The benzene solution of 1-isopropyl-3-azetidinylmethane sulfonate was added dropwise to the stirred refluxing toluene mixture containing the sodium salt of diphenylacetonitrile and refluxing continued for 1.5 hours after addition. The cooled reaction mixture was treated with water, the layers separated, and the organic layer extracted with dilute hydrochloric acid and water. The combined extracts were basified using dilute sodium hydroxide and the base insoluble material extracted with chloroform. The dried extract was concentrated and the residual material was recrystallized from isooctane. The α,α-diphenyl-α-(1-isopropyl-3-azetidinyl)acetonitrile weighed 142 g. (56%) and melted at 93°-95° C.

Analysis: Calcd. for $C_{20}H_{22}N_2$: C,82.72; H,7.64; N,9.65; Found: C,82.72; H,7.73; N,9.55.

PREPARATION 2

α,α-Diphenyl-α-(1-methyl-3-azetidinyl)acetonitrile

A mixture of 4.0 g. (0.11 mole) of sodium amide, 21 g. (0.11 mole) of diphenylacetonitrile and 300 ml. of toluene was stirred at reflux for 4 hours in a nitrogen atmosphere. The heat was removed and an equimolar amount of 3-chloro-1-methylazetidine in toluene was added at a rate which maintained refluxing. The reaction mixture was refluxed an additional 4 hours, allowed to stand overnight at room temperature, washed with water and extracted with dilute hydrochloric acid. The aqueous acid extract was made basic with dilute sodium hydroxide, the base insoluble oil extracted with isopropyl ether, the ether extract dried over sodium sulfate and concentrated. The residual solid was recrystallized from ligroin to give 6.7 g. (27%) of product, m.p. 113°–115° C.

Analysis: Calcd. for $C_{18}H_{18}N_2$: C,82.41; H,6.92; N,10.68; Found: C,82.31; H,6.98; N,10.51.

PREPARATION 3

In the manner of the preceding discussion and in accord with Preparations 1 and 2 starting with the appropriate 1-hydrocarbon-3-azetidinol and diphenylacetonitrile, the following α,α-diphenyl-α-(1-hydrocarbon-3-azetidinyl)acetonitriles are produced:

α,α-diphenyl-α-(1-ethyl-3-azetidinyl)acetonitrile from 1-ethyl-3-azetidinol and diphenylacetonitrile;

α,α-diphenyl-α-(1-propyl-3-azetidinyl)acetonitrile from 1-propyl-3-azetidinol and diphenylacetonitrile;

α,α-diphenyl-α-(1-butyl-3-azetidinyl)acetonitrile from 1-butyl-3-azetidinol and diphenylacetonitrile;

α,α-diphenyl-α-(1-isobutyl-3-azetidinyl)acetonitrile from 1-isobutyl-3-azetidinol and diphenylacetonitrile;

α,α-diphenyl-α-(1-benzyl-3-azetidinyl)acetonitrile from 1-benzyl-3-azetidinol and diphenylacetonitrile; and α,α-diphenyl-α-(1-phenethyl-3-azetidinyl)acetonitrile from 1-phenethyl-3-azetidinol and diphenylacetonitrile.

EXAMPLE 1

4,5-Dihydro-3,3-diphenyl-4-isopropylaminomethylfuran-2-(3H)one

α,α-Diphenyl-α-(1-isopropyl-3-azetidinyl)acetonitrile (142 g.; 0.49 mole) was added to 500 g. of 70% sulfuric acid at 90°–100° C. The temperature was raised to 130° C. for 48 hours. The cooled mixture was poured onto ice and the cold mixture made basic by the addition of solid sodium hydroxide. The basic mixture was extracted with chloroform and the combined chloroform extracts dried over sodium sulfate and concentrated. The residual material was crystallized from an 80% isooctane- 20% isopropyl ether solution. The 4,5-dihydro-3,3-diphenyl-4-isopropylaminomethylfuran-2(3H)one weighed 105 g. (69.3%) and melted at 78°–80° C.

Analysis: Calcd. for $C_{20}H_{23}NO_2$: C,77.64; H,7.49; N,4.53; Found: C,77.68; H,7.36; N,4.23.

EXAMPLE 2

In the manner of the preceding discussion and in accord with Example 1 starting with the appropriate α,α-diphenyl-α-(1-hydrocarbon-3-azetidinyl)acetonitrile and dilute sulfuric acid, the following 4,5-dihydro-3,3-diphenyl-4-hydrocarbylaminomethylfuran-2-(3H)ones are produced:

4,5-dihydro-3,3-diphenyl-4-methylaminomethylfuran-2-(3H)one from α,α-diphenyl-α-(1-methyl-3-azetidinyl)acetonitrile and dilute sulfuric acid;

4,5-dihydro-3,3-diphenyl-4-ethylaminomethylfuran-2-(3H)one from α,α-diphenyl-α-(1-ethyl-3-azetidinyl)acetonitrile and dilute sulfuric acid;

4,5-dihydro-3,3-diphenyl-4-propylaminomethylfuran-2-(3H)one from α,α-diphenyl-α-(1-propyl-3-acetidinyl)acetonitrile and dilute sulfuric acid;

4,5-dihydro-3,3-diphenyl-4-isobutylaminomethylfuran-2-(3H)one from α,α-diphenyl-α-(1-isobutyl-3-azetidinyl)acetonitrile and dilute sulfuric acid;

4,5-dihydro-3,3-diphenyl-4-benzylaminomethylfuran-2-(3H)one from α,α-diphenyl-α-(1-benzyl-3-azetidinyl)acetonitrile and dilute sulfuric acid; and 4,5-dihydro-3,3-diphenyl-4-phenethylaminomethylfuran-2-(3H)one from α,α-diphenyl-α-(1-phenethyl-3-azetidinyl)acetonitrile and dilute sulfuric acid.

EXAMPLE 3

3,3-Diphenyl-4-hydroxymethyl-1-isopropyl-2-pyrrolidinone

Fifty-three grams (0.17 mole) of 4,5-dihydro-3,3-diphenyl-4-isopropylaminomethylfuran-2-(3H)one was dissolved in 300 ml. of boiling isooctane and 0.25 g. of 67% sodium hydride added. After refluxing for 6.5 hours an additional 0.25 g. of 57% sodium hydride was added and refluxing was continued overnight. The cooled mixture was filtered and the solid was recrystallized from toluene. The 3,3-diphenyl-4-hydroxymethyl-1-isopropyl-2-pyrrolidinone weighed 42 g. (80%) and melted at 159°–161° C.

Analysis: Calcd. for $C_{20}H_{23}NO_2$: C,77.64; H,7.49; N,4.53; Found: C,77.71; H,7.52; N,4.37.

EXAMPLE 4

In the manner of the preceding discussion and in accord with Example 3 starting with the appropriate 4,5-dihydro-3,3-diphenyl-4-hydrocarbylaminomethylfuran-2-(3H)one and sodium hydride, the following 3,3-diphenyl-4-hydroxymethyl-1-hydrocarbon-2-pyrrolidinones are produced:

3,3-diphenyl-4-hydroxymethyl-1-methyl-2-pyrrolidinone from 4,5-dihydro-3,3-diphenyl-4-methylaminomethylfuran-2-(3H)one and sodium hydride;

3,3-diphenyl-4-hydroxymethyl-1-ethyl-2-pyrrolidinone from 4,5-dihydro-3,3-diphenyl-4-ethylaminomethylfuran-2-(3H)one and sodium hydride;

3,3-diphenyl-4-hydroxymethyl-1-propyl-2-pyrrolidinone from 4,5-dihydro-3,3-diphenyl-4-propylaminomethylfuran-2-(3H)one and sodium hydride;

3,3-diphenyl-4-hydroxymethyl-1-butyl-2-pyrrolidinone from 4,5-dihydro-3,3-diphenyl-4-butylaminomethylfuran-2-(3H)one and sodium hydride;

3,3-diphenyl-4-hydroxymethyl-1-isobutyl-2-pyrrolidinone from 4,5-dihydro-3,3-diphenyl-4-isobutylaminomethylfuran-2-(3H)one and sodium hydride;

3,3-diphenyl-4-hydroxymethyl-1-benzyl-2-pyrrolidinone from 4,5-dihydro-3,3-diphenyl-4-benzylaminomethylfuran-2-(3H)one and sodium hydride, and 3,3-diphenyl-4-hydroxymethyl-1-phenethyl-2-pyrrolidinone from 4,5-dihydro-3,3-diphenyl-4-phenethylaminomethylfuran-2-(3H)one and sodium hydride.

EXAMPLE 5

4-Chloromethyl-3,3-diphenyl-1-isopropyl-2-pyrrolidinone

A solution of 43 g. (0.14 mole) of 3,3-diphenyl-4-hydroxymethyl-1-isopropyl-2-pyrrolidinone in 250 ml. of chloroform was treated with 33 g. (0.28 mole) of thionyl chloride over a one minute period followed by the dropwise addition of 22 g. (0.23 mole) of pyridine over a 30 minute period. The mixture was refluxed 18 hours and then poured onto ice. The cold mixture was made basic by the addition of sodium hydroxide. The chloroform layer was separated, dried over sodium sulfate and concentrated. The residue was crystallized using charcoal from a 25% ethyl acetate-75% isopropyl ether mixture. The crystalline solid was recrystallized from a 75% ethanol-25% water mixture and then from isopropyl ether. The dried 4-chloromethyl-3,3-diphenyl-1-isopropyl-2-pyrrolidinone weighed 23 g. and melted at 114°-116° C.

Analysis: Calcd. for $C_{20}H_{22}NOCl$: C,73.27; H,6.76; N,4.27; Found: C,73.30; H,6.82; N, 4.22.

I claim:

1. A compound selected from those having the formula

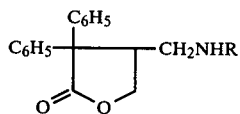

wherein R is selected from the group consisting of lower alkyl having one to six carbon atoms, lower cycloalkyl having four to eight carbon atoms, or phenyl-lower alkyl consisting of benzyl, phenethyl, phenpropyl and α-methylbenzyl.

2. A compound of claim 1 which is 4,5-dihydro-3,3-diphenyl-4-isopropylaminomethylfuran-2(3H)one.

3. A process for the production of a 4,5-dihydro-3,3-diphenyl-4-hydrocarbylaminomethylfuran-2(3H)one which comprises mixing and reacting together an α,α-dihenyl-α-(1-hydrocarbon-3-azetidinyl)acetonitrile and dilute sulfuric acid.

4. A process for the production of a 4,5-dihydrofuran-2-(3H)one having the formula wherein R is selected from the group consisting of lower-alkyl having one to six carbon atoms, lower cycloalkyl having four to eight carbon atoms or phenyllower-alkyl consisting of benzyl, phenethyl and phenpropyl which comprises mixing and reacting together an α,α-diphenyl-α-(1-hydrocarbon-3-azetidinyl)acetonitrile of the formula wherein R is as defined above and dilute sulfuric acid to cause formation of the 4,5-dihydrofuran-2(3H)one.

5. The process according to claim 4 wherein the reactants are heated to accelerate the reaction.

6. The process of claim 4 wherein the dilute sulfuric acid is 70% sulfuric acid.

* * * * *